(12) United States Patent
Higham et al.

(10) Patent No.: US 8,197,547 B2
(45) Date of Patent: Jun. 12, 2012

(54) RADIOVISIBLE HYDROGEL INTERVERTEBRAL DISC NUCLEUS

(75) Inventors: Paul Higham, Ringwood, NJ (US); Chau Ngo, Secaucus, NJ (US); Christopher DeMaria, Glen Rock, NJ (US); Philip F. Williams, III, Teaneck, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1430 days.

(21) Appl. No.: 11/179,387

(22) Filed: Jul. 12, 2005

(65) Prior Publication Data

US 2005/0267583 A1   Dec. 1, 2005

Related U.S. Application Data

(62) Division of application No. 10/244,306, filed on Sep. 16, 2002, now abandoned.

(51) Int. Cl.
*A61F 2/44* (2006.01)
(52) U.S. Cl. .................................. 623/17.16
(58) Field of Classification Search ............ 623/17.11, 623/17.12, 17.16; 606/77; 523/117
See application file for complete search history.

(56) References Cited

U.S. PATENT DOCUMENTS

| | | |
|---|---|---|
| 3,867,728 A | 2/1975 | Stubstad et al. |
| 4,331,783 A | 5/1982 | Stoy |
| 4,337,327 A | 6/1982 | Stoy |
| 4,379,874 A | 4/1983 | Stoy |
| 4,430,083 A | 2/1984 | Ganz et al. |
| 4,631,188 A | 12/1986 | Stoy et al. |
| 4,663,358 A | 5/1987 | Hyon et al. |
| 4,904,260 A | 2/1990 | Ray et al. |
| 4,911,718 A | 3/1990 | Lee et al. |
| 4,916,170 A | 4/1990 | Nambu et al. |
| 4,935,019 A | 6/1990 | Papp, Jr. |
| 5,047,055 A | 9/1991 | Bao et al. |
| 5,084,051 A * | 1/1992 | Tormala et al. .............. 606/77 |
| 5,192,326 A | 3/1993 | Bao |
| 5,300,048 A | 4/1994 | Drewes, Jr. et al. |
| 5,451,393 A | 9/1995 | Liversidge et al. |
| 5,534,028 A | 7/1996 | Bao et al. |

(Continued)

FOREIGN PATENT DOCUMENTS

DE   30 18 966 A1   12/1981

(Continued)

OTHER PUBLICATIONS

North American Spine Society Proceedings, 16th Annual Meeting, Oct. 31, 2001, p. 178-179.

(Continued)

*Primary Examiner* — Brian E. Pellegrino
(74) *Attorney, Agent, or Firm* — Lerner, David, Littenberg, Krumholz & Mentlik, LLP (57) ABSTRACT

A spinal implant for replacing the natural nucleus of the disc made from a polymer such as hydrogel having a radiopaque material located within the polymer. The material may be in the form of a powder dispersed throughout the polymer or may be in he form of a powder dispersed in layers or in other specific locations within the polymer. The radiopaque material is metal such as gold, tungsten, titanium, tantalum or platinum. The metal may also be in the form of a foil or wire located within the hydrogel such as polyurethane, thereby making the implant visible on x-rays. Other polymers besides hydrogel may be used with the radiopaque material being dispersed therein.

21 Claims, 2 Drawing Sheets

U.S. PATENT DOCUMENTS

| | | | |
|---|---|---|---|
| 5,562,736 | A | 10/1996 | Ray et al. |
| 5,607,442 | A | 3/1997 | Fischell et al. |
| 5,674,295 | A | 10/1997 | Ray et al. |
| 5,755,797 | A | 5/1998 | Baumgartner |
| 5,759,174 | A | 6/1998 | Fischell et al. |
| 5,785,642 | A | 7/1998 | Wallace et al. |
| 5,795,922 | A * | 8/1998 | Demian et al. ............ 523/117 |
| 5,800,549 | A | 9/1998 | Bao et al. |
| 5,888,220 | A | 3/1999 | Felt et al. |
| 5,919,235 | A | 7/1999 | Husson et al. |
| 5,976,186 | A | 11/1999 | Bao et al. |
| 6,077,880 | A | 6/2000 | Castillo et al. |
| 6,093,157 | A | 7/2000 | Chandrasekaran |
| 6,113,629 | A | 9/2000 | Ken |
| 6,120,714 | A | 9/2000 | Allan et al. |
| 6,132,465 | A | 10/2000 | Ray et al. |
| 6,176,821 | B1 | 1/2001 | Crocker et al. |
| 6,183,518 | B1 | 2/2001 | Ross et al. |
| 6,187,048 | B1 | 2/2001 | Milner et al. |
| 6,231,615 | B1 | 5/2001 | Preissman |
| 6,280,475 | B1 | 8/2001 | Bao et al. |
| 6,340,367 | B1 | 1/2002 | Stinson et al. |
| 6,595,998 | B2 | 7/2003 | Johnson et al. |
| 6,726,721 | B2 * | 4/2004 | Stoy et al. ............ 623/17.16 |
| 2001/0004710 | A1 | 6/2001 | Felt et al. |
| 2002/0026244 | A1 * | 2/2002 | Trieu ............ 623/17.16 |
| 2005/0267583 | A1 | 12/2005 | Higham et al. |
| 2007/0191946 | A1 | 8/2007 | Heinz et al. |
| 2009/0216317 | A1 | 8/2009 | Cromack et al. |

FOREIGN PATENT DOCUMENTS

| | | |
|---|---|---|
| EP | 0 462 512 A1 | 12/1991 |
| WO | 9726847 | 7/1997 |
| WO | WO-98/55053 | 12/1998 |
| WO | WO-99/62439 | 12/1999 |
| WO | WO-00/03691 | 1/2000 |
| WO | WO-02/17825 A2 | 3/2002 |
| WO | WO-03/045274 | 6/2003 |

OTHER PUBLICATIONS

Horak et al. "New Radiopaque poly-HEMA based hydrogel particles" 1997, vol. 34, pp. 183-188.

Thanoo et al. "Radiopaque hydrogel micrsperes" 1988, vol. 6. No. 2, p. 233-244.

* cited by examiner

RADIOVISIBLE HYDROGEL INTERVERTEBRAL DISC NUCLEUS

BACKGROUND OF THE INVENTION

This application is a divisional of U.S. application Ser. No. 10/244,306, filed on Sep. 16, 2002, the disclosure of which is incorporated herein by reference.

This invention relates to a prosthetic intervertebral disc nucleus. More particularly, it relates to an artificial disc nucleus made of a hydrogel material having a radiovisible material therein.

The intervertebral disc is a complex joint anatomically and functionally. It is composed of three component structures; the nucleus pulposus (the nucleus), the annulus fibrosus (the annulus) and the vertebral end-plates. The biochemical composition and anatomical arrangements within these component structures are related to the biomechanical function of the disc.

The nucleus occupies about 25-40% of the total disc cross-sectional area. It is primarily composed of mucoid material containing mainly proteoglycans with a small amount of collagen. The proteoglycans consist of a protein core with chains of negatively charges keratin sulphate and chondroitin sulphate covalently attached thereto. Due to these constituents, the nucleus is a loose hydrogel which usually contains about 70-90% water by weight. Although the nucleus plays an important role in the biomechanical function of the disc, the mechanical properties of the disc are not well known, largely because of the loose hydrogel nature of the nucleus.

As the nucleus is surrounded by the annulus and vertebral end-plates and the negatively charged sulphate groups are immobilized due to the attachment of these groups to the polymer matrix, the matrix has a higher concentration of counter ions than its surroundings. This ion concentration results in a higher osmotic pressure than the annulus e.g., ranging from about 0.1 to about 0.3 MPa. As a result of the high fixed charge density of the proteoglycan the matrix exerts an osmotic swelling pressure which can support an applied load in much the same way as air pressure in a tire supports the weight of a car.

It is the osmotic swelling pressure and hydrophilicity of the nucleus matrix that offers the nucleus the capability of imbibing fluid until it is balanced with the internal resistance stresses, due to the tensile forces of the collagen network, and the external stresses due to the loads that are applied by muscle and ligament tension. The swelling pressure (Ps) of the nucleus is directly dependent on the concentration and fixed charge densities of proteoglycan, i.e., the higher the concentration and fixed charge densities of proteoglycan the higher will be the swelling pressure of the nucleus. The external pressure changes with posture. When the human body is supine the compressive load on the third lumbar disc is 300 newton (N) which rises to 700 N when an upright stance is assumed. The compressive load increases, yet again, to 1200 N when the body is bent forward by only 20° C. When the external pressure (Pa) increases the previous balance, i.e. Ps=Pa, is upset. To reach a new balance, the swelling pressure has to increase. This increase is achieved by increasing the proteoglycan concentration in the nucleus which is achieved by reducing the fluid in the nucleus. That is why discs lose about 10% of their height, as a result of creep, during the daytime. When the external load is released i.e., Ps is greater than Pa, the nucleus will imbibe fluid from its surroundings in order to reach the new equilibrium value. It is this property of the nucleus that is mainly responsible for the compressive properties of the disc.

The annulus forms the outer limiting boundary of the disc. It is composed of highly structured collagen fibers embedded in an amorphous base substance which is also composed of water and proteoglycans. The amount of proteoglycans is lower in the annulus than in the nucleus. The collagen fibers of the annulus are arranged in concentric laminated bands or lamella, (about 8-12 layers thick) with a thicker anterior wall and thinner posterior wall. In each lamella, the fibers are parallel and attached to the superior and inferior vertebral bodies at an angle of about 30° form the horizontal plane of the disc in both directions. This design particularly resists twisting because the half of the fibers cocked in one direction will tighten as the vertebrae rotate relative to each other in the other direction. The composition of the annulus along the radial axis is not uniform. There is a steady increase in the proportion of collagen from the inner to the outer sections of the annulus. This difference in composition may reflect the need of the inner and outer regions of the annulus to blend into very different tissues while maintaining the strength of the structure. Only the inner lamellae are anchored to the end-plates forming an enclosed vessel for the nucleus. The collagen network of the annulus restrains the tendency of the nucleus gel to absorb water from surrounding tissues and swell. Thus, the collagen fibers in the annulus are always in tension, and the nucleus gel is always in compression.

The two vertebral end-plates are composed of hyaline cartilage, which is a clear, "glassy" tissue, that separates the disc from the adjacent vertebral bodies. This layer acts as a transitional zone between the hard, bony vertebral bodies and the soft disc. Because the intervertebral disc is avascular, most nutrients that the disc needs for metabolism are transported to the disc by diffusion through the end-plate area.

The intervertebral joint exhibits both elastic and viscous behavior. Hence, during the application of a load to the disc there will be an immediate "distortion" or "deformation" of the disc, often referred to as "instantaneous deformation." It has been reported that the major pathway by which water is lost, from the disc during compression, is through the cartilage end-plates. Since the water permeability of the end-plates is in the range of about 0.20 to about $0.85 \times 10^{-17} m^4 N^{-1} sec^{-1}$ it is reasonable to assume that under loading, the initial volume of the disc is constant while the load is applied. Because the natural nucleus of the disc is in the form of a loose hydrogel, i.e., a hydrophilic polymeric material which is insoluble in water, it can be deformed easily, the extent of deformation of the disc being largely dependent on the extensibility of the annulus. It is generally believed that hydrostatic behavior of the nucleus plays an important role in the normal static and dynamic load-sharing capability of the disc and the restoring force of the stretched fibers of the annulus balances the effects of the nucleus swelling pressure. Without the constraint by the annulus, annular bulging of the nucleus would increase considerably. If the load is maintained at a constant level, a gradual change in joint height, commonly referred to as "creep" will occur as a function of time. Eventually, the creep will stabilized and the joint is said to be in "equilibrium." When the load is removed the joint will gradually "recover" to its original height before loading. The creep and relation rates depend on the amount of load applied, the permeability of the end-plates and the water binding capability of the nucleus hydrogel. Creep and relaxation are essential processes in pumping fluid in and out of the disc.

Degeneration of the intervertebral disc is believed to be a common cause of final pathological changes and back pain. As the intervertebral disc ages it undergoes degeneration. The changes that occur are such that, in many respects, the composition of the nucleus seems to approach that of the inner annulus. Intervertebral disc degeneration is, at least in part, the consequence of compositional changes in the nucleus. It has been found that both the molecular weight and the amount of proteoglycans in the nucleus decrease with age, especially in degenerated discs, and the ratio of keratin sulphate to chondroitin sulphate in the nucleus increases. This increase in the ratio of keratin sulphate to chondroitin sulphate and decrease in proteoglycan content decreases the fixed charge density of the nucleus from about 0.28 meq/ml to about 0.18-0.20 meq/ml. These changes cause the nucleus to lose part of its water binding capability which decreases the maximum swelling pressure it can exert. As a result, the maximum water content drops from over about 85%, in preadolescence, to about 70-75% in middle age. The glycosaminoglycan content of prolapsed discs has been found to be lower, and the collagen content higher, than that of normal discs of a comparable age. Discs L-4-L-5 and L-5-S-1 are usually the most degenerated discs.

It is known that although the nucleus only occupies about one third of the total disc area, it takes about 70% of the total loading in a normal disc. Thus, it has been found that the compressive load on the nuclei of moderately degenerated discs is about 30% lower than in comparable normal discs but the compressive load on the annulus increases by 100% in the degenerated discs. This load change is primarily caused by the structural changes in the disc as discussed above. The excess load on the annulus, of the degenerated disc, causes reduction of the disc height and excessive movement of the spinal segments. The flexibility of the disc produces excessive movement of the collagenous fibers which in turn, injures the fiber attachments and causes delamination of the well organized fibers of the annulus ring. The delamination annulus can be further weakened by stress on the annulus and in severe cases this stress will cause tearing of the annulus. This whole process is very similar to driving on a flat tire, where the reinforcement layer will eventually delaminate. Because the thickness of the annulus is not uniform, with the posterior portions being thinner than the anterior portions, delamination and lesions usually occur in the posterior area first.

The spinal disc may also be displaced or damaged due to trauma or diseases. In these cases, and in the case of disc degeneration, the nucleus may herniate and/or protrude into the vertebral canal or intervertebral foramen, in which case it is known as a herniated or "slipped" disc. This disc may in turn press upon the spinal nerve that exits the vertebral canal through the partially obstructed foramen, causing pain or paralysis in the area of its distribution. The most frequent site of occurrence of a herniated disc is in the lower lumbar region. A disc herniation in this area often involves the inferior extremities by compressing the sciatic nerve.

There are basically three types of treatment currently being used for treating low back pain caused by injured or degenerated discs: conservative care, discectomy and fusion. Each of these treatments has its advantages and limitations. The vast majority of patients with low back pain, especially those with first time episodes of low back pain, will get better with conservative treatment. However, it is not necessarily true that conservative care is the most efficient and economical way to solve the low back pain problem.

Discectomy usually provides excellent short term results in relieving the clinical symptoms, by removing the herniated disc material, usually the nucleus, which causes the low back pain either by compressing the spinal nerve or by chemical irritation. Clearly, a discectomy is not desirable from a biomechanical point of view. In a healthy disc, the nucleus takes the most compressional load and in a degenerated disc this load is primarily distributed onto the annulus ring which, as described above, causes tearing and delamination of the annulus. Removal of the nucleus in a discectomy actually causes distribution the compressive load onto the annulus ring thereby narrowing the disc spaces. It has been reported that a long-term disc height decrease might be expected to cause irreversible osteoarthritis-like changed in the facet joint. That is why discectomy yields poor long term benefits and results in a high incidence of reherniation.

Fusion generally does a good job in eliminating symptoms and stabilizing the joint. However, because the motion of the fused segment is restricted, the range of motion of the adjoining vertebral discs is increased possibly enhancing their degenerative processes.

Because of these disadvantages, it is desirable to use a prosthetic joint device which not only is able to replace the injured or degenerated intervertebral disc, but also can mimic the physiological and the biomechanical function of the replaced disc and prevent further degeneration of the surrounding tissue.

Artificial discs are well known in the prior art. U.S. Pat. No. 3,867,728, to Stubstad et al., relates to a device which replaces the entire disc. This device is made by laminating vertical, horizontal or axial sheets of elastic polymer. U.S. Pat. No. 4,309,777, to Patil, relates to a prosthetic utilizing metal springs and cups. A spinal implant comprising a rigid solid body having a porous coating on part of its surface is shown in Kenna's U.S. Pat. No. 4,714,469. An intervertebral disc prosthetic consisting of a pair of rigid plugs to replace the degenerated disc is referred by Kuntz, U.S. Pat. No. 4,349,921. U.S. Pat. Nos. 4,772,287 and 4,904,260 to Ray et al., teach the use of a pair of cylindrical prosthetic intervertebral disc capsules with or without therapeutical agents. U.S. Pat. No. 4,911,718 to Lee et al., relates to an elastomeric disc spacer comprising three different parts; nucleus, annulus and end-plates, of different materials. At the present time, none of these inventions has become a product in the spinal care market. Bao et al., in U.S. Pat. Nos. 5,047,055 and 5,192,326 (assigned to the assignee of this invention and incorporated herein by reference) describe artificial nuclei comprising hydrogels in the form of large pieces shaped when fully hydrated, to generally conform to the disc cavity or hydrogel beads within a porous envelope, respectively. The hydrogels have an equilibrium water content (EWC) of at least about 30% and a compressive strength of at least about 1 meganewtons per square meter (1 $MNm^{-2}$) when subjected to the constraints of the annulus and end plates of the disc. Preferably, the compressive strength of the nucleus is about 4 $MNm^{-2}$ or even higher.

The primary disadvantage of the invention of Substad et al., Patil, Kenna and Lee et al., is that use of their prosthesis requires complete replacement of the natural disc which involves numerous surgical difficulties. Secondly, the intervertebral disc is a complex joint, anatomically and functionally, comprising the aforementioned three component structures, each of which has its own unique structural characteristics. Designing and fabricating such a complicated prosthesis from acceptable materials, which will mimic the function of the natural disc, is very difficult. A further problem is the difficulty of preventing the prosthesis from dislodging. Fourthly, even for prostheses which are only intended for replacing the nucleus, a major obstacle has been to find a material which is similar to the natural and is also able to restore the normal function of the nucleus. Hydrophobic elastomers and thermoplastic polymers are not desirable for use in the prosthetic nuclei due to their significant inherent differences from the natural nucleus e.g., lack of hydrophilicty, in the elastomers, and lack of flexibility in their thermoplasts.

These problems are not solved by Kuntz, who uses elastic rubber plugs, or by Froning and Ray et al., who use bladders, or capsules, respectively, which are filled with a fluid or thixotropic gel. According to the Ray and Froning patents, liquid was used to fill the capsules and bladders, respectively, thereby requiring that their membranes be completely sealed to prevent fluid leakage. As a consequence, those devices cannot completely restore the function of the nucleus which allows body fluid to diffuse in and out during cyclic loading thereby providing the nutrients the disc needs.

The Bao et al., prosthetic lumbar disc nuclei are made from hydrogels. Hydrogels have been used in biomedical applications, such as contact lenses. Among the advantages of hydrogels is that they are more biocompatible than hydrophobic elastomers and metals. This biocompatibility is largely due to the unique characteristics of hydrogels in that they are soft and contain water like the surround tissues and have relatively low frictional coefficients with respect to the surrounding tissues. The biocompatibility of hydrogels results in prosthetic nuclei which are more easily tolerated in the body. Furthermore, hydrophobic elastomeric and metallic gels will not permit diffusion of aqueous compositions, and their solutes, therethrough.

An additional advantage of some hydrogels is their good mechanical strength which permits them to withstand the load on the disc and restore the normal space between the vertebral bodies. The aforementioned nuclei of Bao et al. have high mechanical strength and are able to withstand the body loads and assist in the healing of the defective annuli.

Other advantages of the hydrogels, used in Bao et al. nuclei, are their excellent viscoelastic properties and shape memory. Hydrogels contain a large amount of water which acts as a plasticizer. Part of the water is available as free water which has more freedom to leave the hydrogel when the hydrogel is partially dehydrated under mechanical pressure. This characteristic of the hydrogels enables them to creep, in the same way as the natural nucleus, under compression and to withstand cyclic loading for long periods without any significant degradation or loss of their elasticity. This is because water in the hydrogel behaves like a cushion whereby the polymeric network of a hydrogel with a high equilibrium water content (EWC) is less susceptible to damage under mechanical load.

Another advantage of hydrogels is their permeability to water and water-soluble substances, such as nutrients, metabolites and the like. It is know that body fluid diffusion, under cycle loading, is the major source of nutrients to the natural disc. If the route of this nutrient diffusion is blocked, e.g., by a water-impermeable nucleus, further deterioration of the disc will ensure.

Hydrogels can be dehydrated and the resultant xerogels hydrated again without changing the properties of the hydrogels. When a hydrogel is dehydrated, its volume decreases, thereby facilitating implantation of the prosthetic nucleus into the nuclear cavity in the disc. The implanted prosthetic nucleus will then swell, in the body, by absorption of body fluid up to its EWC. The EWC of the hydrogel depends on the compressive load applied thereto. Thus, the EWC of a specific hydrogel in an open container will differ from the EWC of the same hydrogel in a closed vessel such as an intervertebral disc. The EWC values, referred to below, are for hydrogels subjected to compressive loads under the conditions found in an intervertebral disc. The expansion factor of a dehydrated hydrogel, in turn, is dependent on its EWC. Thus, it may vary from 1.19 for a hydrogel of 38% EWC to 1.73 for a hydrogel of 80% EWC. For an 80% EWC hydrogel, the volume of the dehydrated prosthetic nucleus is usually about 20% of that of the hydrated one. The ability to be dehydrated and then return to its original shape upon hydration, up to its EWC, makes it possible to implant the device posterior-laterally during surgery, thereby reducing the complexity and risk of intraspinal surgery as traditionally used. The danger of perforation of the nerve, dural sac, arteries and other organs is also reduced. In addition, the incision area on the annulus can be reduced, thereby helping to heal the annulus and prevent the reherniation of the disc. Hydrogels are also useful for drug delivery into the disc due to their capability for controlled release of drugs. Various therapeutic agents, such as growth factors, long term analgesics and anti-inflammatory agents can attach to the prosthetic nucleus and be released in a controllable rate after implantation of the nucleus in the disc.

Furthermore, dimensional integrity can be maintained with hydrogels having a water content of up to about 90%. This dimensional integrity, if the nucleus is properly designed will aid in distributing the vertebral load to a larger area on the annulus ring and prevent the prosthetic nucleus from bulging and herniating.

However, it is normally difficult to implant a fully hydrated hydrogel prosthesis in the cavity, of a disc, through the small window provided in the disc, for removing the herniated nucleus, especially in a percutaneous surgery by virtue of their bulkiness in a fully in a fully hydrated state. Therefore, such prosthesis must be implanted, in the disc in relatively dehydrated states which requires long periods to achieve their EWCs due to their low surface areas. Other hydrogels, having high surface areas, do not completely conform to the shape of the nuclear cavity. Other polymers such as those disclosed in WO 97/268407 (PCT/US97 00457), the teachings of which are incorporated herein by reference, can also be used to fill the disc nucleus.

It is desirable to provide a hydrogel implant which is inherently radiopaque, i.e., radiovisible so that surgeons could view the placement of the implant in the cavity produced by the removal of a spinal nucleus. It is advantageous if the radiovisible material could be incorporated into the polymeric or hydrogel material making up the prosthetic nucleus implant. It is desirable to have a method of making the hydrogel or polymer radiopaque which would allow dimensional changes in the hydrogel implant during processing and after implantation without compromising the mechanical integrity of the implant.

Various methods are used to implant a hydrogel or other polymeric nucleus implant. Such a method is shown in U.S. Pat. No. 5,800,549, the teachings of which are incorporated herein by reference.

SUMMARY OF THE INVENTION

It is an object of the invention to provide a novel hydrogel or other polymeric implant for replacing the resected natural nucleus of a spinal disc.

It is a further object of the invention to provide a novel hydrogel or other polymeric prosthetic nucleus which has radiovisible material contained therein.

It is yet a further object of the invention to provide a method for incorporating radiovisible material within the hydrogel or polymer either dispersed throughout the implant or in discreet locations therein.

Such objects are achieved by the spinal implant for replacing the natural nucleus of the disc made of a hydrogel having radiovisible material located within the hydrogel. The material may be a metal such as gold, tungsten, tantalum, platinum, titanium or combinations thereof.

The material may be in powder form and may be distributed throughout the hydrogel in a uniform manner or may be in powder form and placed in the hydrogel or polymeric implant in discreet layers or locations. The radiopaque powder preferably has a maximum diameter of between 10 and 100 μm and more preferably the powder has a diameter of about 75 μm.

Alternately, the metal may be in the form of foil, either in strip form in the form of flakes scattered throughout the implant. If the foil is in strip form, it should be relatively thin, i.e., in the range of 1-100 μm thick so that when used with a hydrogel, it expands and contracts as the hydrogel is hydrated and dehydrated. In the preferred embodiment, a thickness at the lower end of this range is desirable, for example, 2 μm thick.

In an additional embodiment, the implant may be in the form of a metal wire or coil placed in the hydrogel implant during its formation. Again, the wire is of such a diameter as to be able to fold upon itself during hydration and dehydration of the hydrogel.

If the polymer used is formed in situ then the metal that imparts radiovisibility to the implant is dispersed throughout the polymer prior to injection and curing.

If the polymer is processed in the melt then the metal is blended into the polymer when it is above its melt temperature.

Methods of making the hydrogel, including the radiopaque material, include dissolving the polymer powder to form a homogeneous solution and then mixing the metal powder with metal flakes therein while the solution is still a liquid and then freezing the solution to form a solid. Usually the solution is poured into a mold to form the hydrogel and then the mold is placed in the freezer.

Alternately, the hydrogel implant can be formed sequentially by placing a homogeneous solution with radiopaque material in the mold but filling only a portion of the mold, freezing the solution, placing an additional layer of hydrogel, including the radiopaque metal upon the first layer of solidified hydrogel and thereafter freezing the second layer to form a solid. This process may be repeated to form alternate layers in the prosthetic nucleus which are either radialucent or radiopaque.

In yet another embodiment, the polymeric implant can be formed by melting a polymer such as poly(acrylonitrile) and blending the radiopacifying agent prior to molding the implant. Sequential molding operations performed on one implant can result in the radiopacifying agent being localized into discreet areas of the implant. The polymeric implant can also be formed by injecting both a crosslinkable material (e.g. monomer and/or prepolymer) and a crosslinking agent, and then allowing the crosslinkable material to cure in situ such as polyurethane. Radiovisibility can be imparted to this implant by adding the radiopacifying agent to the crosslinkable material, the crosslinking agent, or both.

If a coil or foil is used to produce the radiopaque portions of the hydrogel, the foil or coil may be placed in the liquid hydrogel prior to solidifying it by cooling.

DETAILED DESCRIPTION

Figure 1:
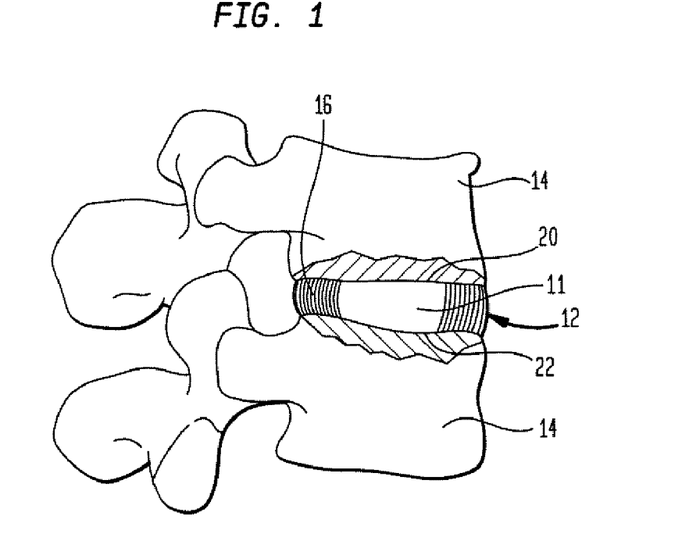
FIG. 1 is an elevational view of the vertebral disc absent its nucleus with its associated vertebra.
Figure 2:
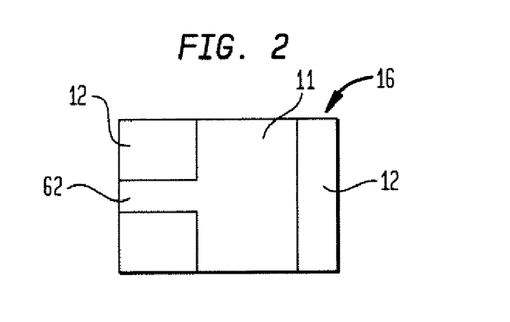
FIG. 2 is an elevated view of the intervertebral disc and associated vertebra of FIG. 1 from which the nucleus has been removed.

Referring to FIGS. 1 through 6, in the preferred embodiment the hydrogel prosthetic nucleus of the present invention, generally denoted as 10, conforms when hydrated to its EWC, generally to the shape of the natural nucleus. Alternately, the hydrogel can be constrained in a polymer jacket. Such is taught in U.S. Pat. Nos. 5,674,295 and 6,132,465. The prosthetic nucleus is implanted within cavity 11 the disc 12 of the vertebrae 14 and is surrounded by the natural annulus 16. Vertebral end plates 20 and 22, as shown in FIG. 1, cover the superior and inferior faces of nucleus 10 respectively. The implant is inserted through an opening 62 in annulus 12.

Figure 3:
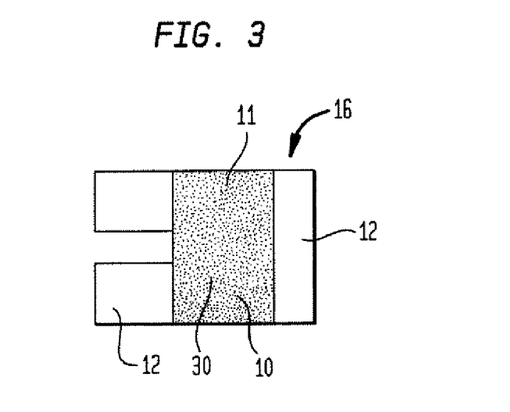
FIG. 3 is an elevational view of the disc of FIG. 2 with the polymeric nucleus of the present invention implanted therein showing a radiopaque powder dispersed throughout the implant.

Referring to FIG. 3, there is shown the prosthetic nucleus of the present invention, including metal particles 30 dispersed uniformly throughout. Uniformly is used in a relative sense not to indicate that the particles are exactly spaced within the hydrogel.

Figure 4:
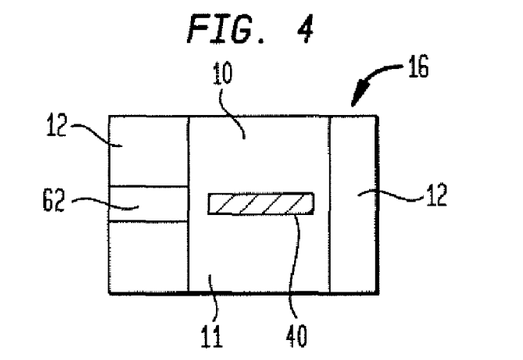
FIG. 4 is an elevational view of the disc of FIG. 2 with a polymeric implant having a foil strip therein.

Referring to FIG. 4, there is shown the prosthetic disc nucleus of the present invention with a radiopaque foil strip 40 located therein.

Figure 5:
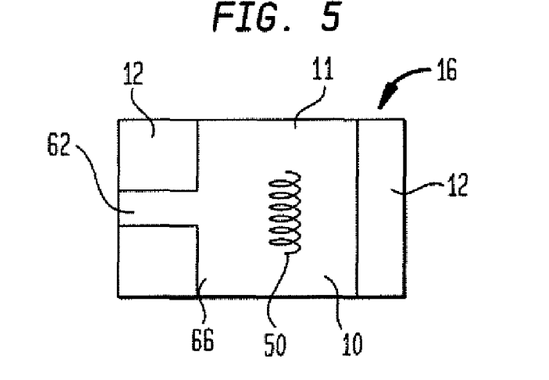
FIG. 5 is an elevational view of the disc space of FIG. 2 with a polymeric implant having a metal coil therein.

Referring to FIG. 5, there is shown a polymeric implant of the present invention having a radiopaque or radiovisible coil 50 located therein.

Figure 6:
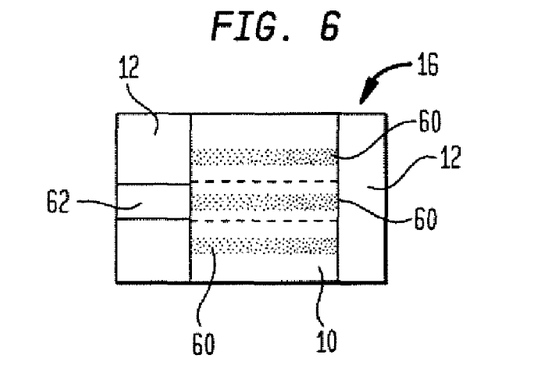
FIG. 6 is an elevational view of the disc of FIG. 2 having a polymeric implant, including seven layers with three layers including radiopaque metal powder dispersed therethrough.

Referring to FIG. 6, there is shown a prosthetic disc nucleus 10 of the present invention having radiopaque layers of metal particles or foil particles 60 located therein. While three layers are shown in FIG. 6, one layer or two layers or more than three layers may be utilized. As shown in FIG. 6, the three layers 60 having the radiopaque powder or particles extend across the entire distance between the inner walls of cavity 11 of annulus 16 of disc 12. These layers are sandwiched between two layers having no radiopaque particles. This structure results from the method of manufacturing nucleus 10 as set forth in Example 2 below.

Hydrogels useful in the practice of the invention include lightly cross-linked biocompatible homopolymers and copolymers of hydrophilic monomers such as 2-hydroxylalkyl acrylates and methacrylates, e.g., 2-hydroxyethyl methacrylate (HEMA); N-vinyl monomers, for example, N-vinyl-2-pyyrolidone (N-VP); ethylenically unsaturated acids, for example, methacrylic acid (MA) and ethylenically unsaturated bases such as 2-(diethylamino) ethyl methacrylate (DE-AEMA). The copolymers may further include residues from non-hydrophilic monomers such as alkyl methacrylates, for example, methyl methacrylate (MMA), and the like. The cross-linked polymers are formed, by known methods, in the presence of cross-linking agents, such as ethyleneglycol dimethacrylate and methylenebis (acrylamide), and initiators such as 2,2-azobis (isobutyronitrile), benzoyl peroxide, and the like, and radiation such as UV and γ-ray.

Methods for the preparation of these polymers and copolymers is well known to the art. The EWC of these hydrogels can vary, e.g., from about 38% for Polymacon™ (poly HEMA) to about 79% for Lidofilcon™ B (a copolymer of N-VP and MMA) under ambient conditions.

Another type of hydrogel, useful in the practice of the invention, is illustrated by HYPAN™ and poly(vinyl alcohol) (PVA) hydrogels. These hydrogels, unlike the aforementioned hydrogels, are not cross-linked. Their insolubility in aqueous media is due to their partially crystalline structures. HYPAN™ is a partially hydrolyzed polyacrylonitrile. It has a multiblock copolymer (MBC) structure comprising hard crystalline nitrile blocks, which provide the hydrogel with good mechanical properties, and soft amorphous hydrophilic blocks to provide the hydrogel with good water binding capability. The methods of preparing HYPAN™ hydrogels of different water contents and mechanical properties have been disclosed in the U.S. Pat. Nos. 4,337,327, 4,370,451, 4,331,783, 4,369,294, 4,420,589, 4,379,874 and 4,631,188. The pre-nuclear forms of this material, for use in this invention, can be prepared by melt processing using solvents such as DMF and DMSO, as melting aids or by solution processing.

Other types of polymers useful in the practice of the invention include medical grade polyurethanes and materials formed by crosslinking protein precursors. These materials may or may not form hydrogels in their final form but are still useful as materials to form prosthetic nucleus replacements. Such materials are shown in U.S. Pat. Nos. 5,888,220, 6,189,048, 6,183,518 and in Publication U.S. 20020049498 A1, the teachings of which are incorporated herein by reference.

A preferred hydrogel for use in the practice of this invention is highly hydrolyzed crystalline poly (vinyl alcohol) (PVA). The amount of hydrolyzation may be between 95 and 100 percent depending on the desired EWC which will be from about 60% to about 90%. Generally, the final hydrogel water content increases with decreasing hydrolyzation of the initial PVA which results in decreased crystallinity.

Partially crystalline PVA hydrogels may be prepared, from commercially available PVA powders, by any of the methods disclosed in the U.S. Pat. No. 4,663,358, the teachings of which are incorporated herein by reference. Typically, 10-15% PVA powder is mixed with a solvent, such as water, dimethyl sulfoxide (DMSO), ethylene glycol and mixtures thereof. A preferred solvent is 15% water in DMSO. The mixture is then heated at a temperature of about 100 to about 120° C., until a viscous solution is formed. The solution is then poured or injected into a tubular metal, glass or plastic mold and allowed to cool to below −10° C., preferably about −20° C.

The solution is maintained at the temperature for several hours, preferably about 20 hours, during which time crystallization and, therefore, gelation of the PVA occurs. The shaped gel is soaked with several portions of water which are periodically replaced, over a period of at least two days, until all the organic solvent in the gel has been replaced by water. The hydrated gel can then be partially or completely dehydrated for implantation. The hydrogels thus prepared have EWC's between 60-90% and compressive strengths of at least 1 $MNm^{-2}$, preferably about 4 $MNm^{-2}$, when subject to the same constraints as the natural nucleus in an intervertebral disc. In general, any polymer that can be used for biomedical purposes can be used as long as the polymer exhibits the desired stiffness characteristics.

Completion of the solvent exchange is determined by known methods. For instance, when the solvent is DMSO its removal, from the gel, is determined as follows:

50 μL of a 0.01 N $KMnO_4$ are added to 50 mL aliquots of the water which has been separated from the gels. The presence of DMSO, in the water, will be indicated by disappearance of the characteristic pink color of the $KMnO_4$. When the DMSO has been completely removed, the pink color will not disappear. This method has a detection limit of 0.3 ppm, for DMSO, when compared to a blank and 0.3 ppm aqueous DMSO standard.

In general, any hydrogel that can be used for biomedical purposes can be used as long as the hydrogel exhibits an EWC from about 30 to 90% and a compressive strength of at least about 1 $MNm^{-2}$, preferably 4 $MNm^{-2}$, when subjected to the constraints of the annulus and end plates of the disc. A rod or tube made from these materials, in a dehydrated form, i.e., as xerogels, can be prepared either by cast molding or lathe cutting. In cast molding, the liquid monomer mixture, with initiator, is poured into a mold of predetermined shape and size, and cured. If desired, the casting mixture may include water, or another aqueous medium. Under those circumstances the resultant rod or tube will be partially hydrated, i.e., a hydrogel. In the case of lathe cutting, the xerogel can be prepared, in a similar manner to the above, in the form of a block or rod which is larger than needed to form the prosthetic nucleus. The xerogel is then cut to the shape and size required for implantation into the disc cavity. In both cases, the hydrogel expansion factor, due to polymer swelling upon hydration, has to be taken into account in designing the mold or in cutting the block, rod or tube.

The exact size of the prosthetic nucleus, at its EWC, can be varied for different individuals. A typical size of an adult nucleus is about 2 cm in the semi-minor axis, about 4 cm in the semi-major axis and about 1.2 cm in thickness.

Polymers curable within the body can also be used to replace the natural nucleus and strengthen the annulus which is made of cartilage. Natural cartilage is a non-vascular structure found in various parts of the body. Articular cartilage tends to exist as a finely granular matrix forming a thick incrustation on the surfaces of joints. The natural elasticity of articular cartilage enables it to break the force of concussions, while its smoothness affords ease and freedom of movement. Preferred biomaterials, therefore, are intended to mimic many of the physical-chemical characteristics of natural cartilage. Biomaterials can be provided as one component systems, or as two or more component systems that can be mixed prior to or during delivery, or at the site of repair. Generally such biomaterials are flowable in their uncured form, meaning they are of sufficient viscosity to allow their delivery through a cannula of on the order of about 2 mm to about 6 mm inner diameter, and preferably of about 3 mm to about 5 mm inner diameter. Such biomaterials are also curable, meaning that they can be cured or otherwise modified, in situ, at the tissue site, in order to undergo a phase or chemical change sufficient to retain a desired position and configuration.

When cured, preferred materials can be homogenous (i.e., providing the same chemical-physical parameters throughout), or they can be heterogenous. An example of a heterogenous biomaterial for use as a disc replacement is a biomaterial that mimics the natural disc by providing a more rigid outer envelope (akin to the annulus) and a more liquid interior core (akin to the nucleus). In an alternative embodiment, biomaterials can be used that provide implants having varying regions of varying or different physical-chemical properties. With disc replacement, for instance, biomaterials can be used to provide a more rigid, annulus-like outer region, and a more fluid, nucleus-like core. Such di- or higher phasic cured materials can be prepared by the use of a single biomaterial, e.g., one that undergoes varying states of cure, or by using a plurality of biomaterials. Examples of suitable biomaterials includes, but are not limited to, polyurethane polymers.

The in situ cured polymer may comprise a thermosetting polyurethane polymer based on a suitable combination of isocyanates, long chain polyols and short chain (low molecular weight) extenders and/or crosslinkers. Suitable components are commercially available and are each preferably used in the highest possible grade, e.g., reagent or preferably analytical grade or higher. Examples of suitable isocyanates include 4,4'-diphenyl methane diisocyanate ("MDI"), and 4,2'-diphenylmethane diisocyanate ("TDI"). Examples of suitable long chain polyols include tetrahydrofuran polymers such as poly(tetramethylene oxide) ("PTMO"). Particularly preferred are combinations of PTMO's having molecular weights of 250 and 1000, in ratios of between about 1 to 1 and about 1 to 3 parts, respectively. Examples of suitable extenders/crosslinkers include 1,4-butanediol and trimethylol propane, and blends thereof, preferably used at a ratio of between about 1 to 1 and about 1 to 7 parts, respectively. Such performance can be evaluated using procedures commonly accepted for the evaluation of natural tissue and joints, as well as the elevation of biomaterials.

In particular, the in situ cured polymer forms, exhibit mechanical properties that approximate those of the natural tissue that they are intended to replace. For instance, for load bearing applications, preferred cured composites exhibit a load bearing strength of between about 50 and about 200 psi (pounds per square inch), and preferably between about 100 and about 150 psi. Such composites also exhibit a shear stress of between about 10 and 100 psi, and preferably between about 30 and 50 psi, as such units are typically determined in the evaluation of natural tissue and joints.

Biomaterials provided as a plurality of components, e.g., a two-part polyurethane system, can be mixed with the radiopaque or radiovisible metal powder at the time of use using suitable mixing techniques, such as those commonly used for the delivery of two-parts adhesive formulations. More preferably, the metal powder can be added during melt processing of the polymer. A suitable mixing device involves, for instance, a static mixer having a hollow tube having a segmented, helical vein running through its lumen. A two-part polyurethane system can be mixed by forcing the respective components through a lumen, under pressure.

The hydrogels and polymers of the present invention have a much higher structural integrity than the natural nucleus, i.e., they are deformed with greater difficulty under a mechanical compressive load (shaped gel vs. loose gel). That is because, unlike the loose gel of the natural nucleus, the shaped gel has shape memory due to the cross-linking or strong hydrogen bonding in the polymer matrix. However, it would still have extensive lateral bulging under high compressive load if there were no boundaries to constrain the deformation. Because use of the prevent invention does not involve removal of the disc annulus and/or end-plates, the lateral bulging of the hydrogel nucleus will be restricted by the restoring forces of the stretch fibers. Also, due to its superior structural integrity, the hydrogel nucleus will not herniate or bulge through the previously herniated areas or the incision which was made to remove the degenerated nucleus.

If a hydrogel is used, since the natural nucleus is also primarily, a hydrogel, the implanted prosthetic nucleus can easily restore all the biomechanical functions of the nucleus which had been removed. Unlike the prior art prosthetic discs, the hydrogel nucleus of the present invention will restore the viscoelastic behavior of the disc due to the water binding capability of the prosthetic hydrogel.

The implantation of a prosthetic nucleus 10 can be performed in conjunction with a discectomy or chemonuclealysis. Because the properties of the prosthetic nucleus of the present invention are similar to those of the nucleus material, the herniated nucleus can be partially or totally replaced by the hydrogel prosthetic nucleus. Due to the small size of the prosthetic it can be implanted into the disc by means of a posterior lateral approach, thereby significantly reducing the difficulty and the risk of the operation.

The volume of a hydrogel nucleus of about 80% EWC will be reduced by about 80% (to about 20% of its original volume) when dehydrated. Consequently, the surgeon does not need to jack apart the vertebrae adjacent to a damaged disc as required by, for example, the device disclosed in U.S. Pat. No. 4,772,287. The height of the dehydrated prosthetic nucleus, when inserted, is smaller than the disc space. Furthermore, the rigidity of the dehydrated prosthetic nucleus will help the surgeons to manipulate the prosthetic nucleus during the operation. After implantation, the hydrogel nucleus of the present invention swells in the body to a predetermined height which is enough to maintain the space between the vertebral body. The swelling process normally takes several hours to two days depending on the size of the prosthetic nucleus and type of hydrogel.

The preferred method for making the radiopaque hydrogel or polymer involves incorporating a metallic element into the structure of the implant. The metallic element is in a form that will allow it move with the polymeric structure as the implant changes dimensions and/or geometry. This property is important because it minimizes any internal stress amplification that could be caused by incorporating the metallic component into the dynamic (i.e. non-fusion) spine implant.

Three embodiments of the invention are described. The first embodiment involves incorporating radiopaque materials such as a metal powder, for example, gold or tungsten, into the polymer while it is a liquid either due to the use of solvents, heat if the polymer can be processed in the melt, or is in a pre-polymer form prior to a curing step. The metal powder has a nominal diameter of 10-100 μm, with a preferred maximum size of 75 μm. The powder is incorporated into the liquid polymer solution/melt preferably in a concentration between 0.02 and 0.5 g per cc of polymer, with a preferred concentration of 0.1 g/cc. The powder may be evenly dispersed throughout the entire implant, or incorporated into the implant in specific areas only. For example, by combining the use of liquid-phase polymer that contains no metal powder in a mold with liquid polymer that does contain metal powder it is possible to form radiovisible areas of an implant in a variety of geometries (e.g. lines, discs, spheres). An embodiment of the layered polymeric implant has one or more planes in the implant comprised of the radiovisible polymer. It is possible to incorporate 1 to 5 or more bands of powder-filled polymer in any plane across an implant that also has polymer regions where no metal powder exits using techniques that prevent the powder from migrating until the liquid-phase polymer has formed a solid, as discussed below or creating an even dispersion of metal powder throughout the entire implant.

A second embodiment involves the use of a metal foil 0.001 to 0.1 mm thick for example gold, tantalum or tungsten foil. The foil can be placed into the liquid polymer in the form of sheets or strips, or it can be chopped into small pieces and incorporated into the implant in the manner described for metal powders. Small pieces of foil may provide an advantage for some polymer systems with a lower viscosity in the liquid phase because each piece may have less mass than a metal particle, which would result in less tendency for migration through the liquid-phase polymer. In addition, the geometry of a piece of foil with multiple irregular folds may also have less tendency to migrate through liquid-phase polymer than, for example, a smoother spherical particle. Examples include suspending 1 to 5 or more strips of metal foil in any plane in the implant, or incorporating 1 to 5 or more bands of polymer that contain small pieces of chopped foil that may or may not be "crinkled" as described above for powder, and creating an even dispersion of pieces of chopped metal foil that may or may not be "crinkled" throughout the implant.

A third embodiment involves the use of a metal wire or coil, preferably 0.01 to 1.0 mm in length, for example, gold wire, tungsten wire or platinum wire. The metal wire is suspended in the liquid-phase polymer in such a manner that the wire will be completely encapsulated by solid polymer at the end of the manufacturing process. Alternatively, the wire can be formed into a coil or other shape that may provide better radiographic information about the implant and have less of an ability to migrate through the solid polymer. Examples include suspending 1 to 5 or more pieces of wire in the liquid-phase polymer in such a way as they will not be exposed to the surface of the implant, or incorporating 1 to 5 or more bands of polymer that contain small pieces of chopped wire or creating an even dispersion of pieces of chopped metal wire throughout the implant using techniques as described below.

EXAMPLE I

A PVA solution was formed by mixing 15 g of PVA powder (Kuraray 117 or equivalent), having a molecular weight about 78000 and about 99.7% hydrolysed (Cat. No. 15129, Polysciences Inc., Warrington, Pa.), with 85 ml of a solvent comprising 15% water in DMSO. The mixture was heated at about 110° C. until a homogenous viscous solution formed.

EXAMPLE II 0.1 gram of gold powder (maximum diameter 75 μm) per cc of liquid-phase of PVA solution of Example I were mixed. The two ingredients were combined in the following manner to create a metal-filled polymer solution. A plunger from a 5 cc first syringe was removed and the first syringe was slowly filled half way with PVA solution, 0.5 g of the gold powder was poured into the syringe. The first syringe was then completely filled with PVA solution, and the plunger replaced. A two-way luer connector was screwed onto the tip of the first syringe and the connector was primed with PVA solution from the syringe. The first syringe and a second syringe of equal size were connected using the connector. The gold powder solution from the first syringe was squeezed into the empty syringe. This was repeated until the solution was uniformly mixed. A third syringe was filled with PVA solution without any gold. 5 cc of the PVA solution of the third syringe was injected into a nucleus mold having a total volume of about 20 cc and a diameter of about 1.5 cm. The mold was cooled down in freezer (4° C.) for about 20 minutes. 1 cc of gold powder-filled PVA solution was injected on top of the cooled solution in the mold. 9 cc of the PVA solution was slowly injected into the mold, on top of the gold powder solution. The mold was again cooled down in the freezer for about 15 minutes. About 5 cc of gold powder-filled solution was again injected on top of the cooled solution in the mold to form a second radiopaque layer. The mold was then completely filled with the PVA solution from the third syringe.

EXAMPLE III

About 20 cc of the gold solution was prepared as described in Example II using two 20 cc syringes and 2 grams of gold powder. The metal filled polymer solution was slowly injected into a 20 cc implant mold (for a #5 size implant), filling the mold completely. The mold reservoir was capped so that the metal-filled PVA solution will not leak out of the mold if the mold is inverted. The mold was pressurized and placed in a Turbula Mixer which was placed into a programmable freezer. The mixer used must be able to both rotate and tip the mold during gelation of the metal filled PVA solution to keep the powder in the solution uniformly distributed. The mixer can rotate the mold about a central axis, tilt the mold back and forth through a 90° arc about an axis perpendicular to the central axis. This kept the metal particles uniformly suspended in the solution until it gelled.

EXAMPLE IV

The PVA solution prepared for the third syringe of Example II without the gold powder was used in this Example. A strip of gold metal foil was suspended in an empty mold using a thin monofilament of nylon so that the strip is positioned in approximately the center of the mold. The nylon filament was smooth and non-porous. The mold was slowly filled with the PVA solution. The mold was then placed in the freezer and after completing the process, the monofilament was pulled out of the implant leaving the strip of metal foil intact.

EXAMPLE V

The gold foil of Example IV was cut into small pieces using a food processor or other convenient method to create metal flakes. 0.03 g of metal flakes per cc of the liquid phase polymer of Example I. 20 cc of solution were placed in a mold and the solution was then frozen as above to form the implant.

EXAMPLE VI

A gold coil was suspended in an empty 20 cc mold using a thin monofilament so that the coil is positioned in approximately the center of the mold. The filament was smooth and non-porous. A barb fitting through a small loop at the top of the metal coil is a convenient way to attach the filament and the coil. Slowly fill the molds with the PVA solution of Example I. After completing the gelation process by freezing, the monofilament was pulled out of the implant leaving the gold coil intact.

After gelation, the implants were sterilized as described in my Ion Treated Hydrogel copending application, U.S. Ser. No. 10/020,389 and then packaged.

The implants are formed into 10 different sizes by volume with a size range of 1.1 to 5.2 cc for future implantation.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal implant for replacing the natural nucleus of a disc comprising:
   a layered hydrogel material with at least one layer of the hydrogel material having powdered radiopaque material therein, the implant having an uppermost and lowermost surface and outer side surfaces which contact a disc annulus extending therebetween; and
   the powdered radiopaque material incorporated into the at least one layer of the hydrogel material in the form of at least one discrete planar layer, an upper and lower side of the at least one discrete planar layer including radiopaque powder contacts a layer of the hydrogel material not containing radiopaque powder, the at least one planar layer containing radiopaque powder extends the entire length of the layer to the outer side surfaces of the implant which contact the disc annulus, the powdered radiopaque material in the at least one hydrogel layer having radiopaque material are in a concentration of less than 0.5 gram of radiopaque powdered material to 1 gram of hydrogel and moves with the hydrogel body as the body changes dimensions and geometry under load, the upper and lowermost layers of the implant having no radiopaque powder.

2. The spinal implant as set forth in claim 1 wherein there are between 2 and 5 discrete planar layers of the hydrogel containing the radiopaque powder in the implant body oriented in parallel planes between the upper and lowermost layers of the implant.

3. The spinal implant as set forth in claim 2 wherein the radiopaque material is metal particles.

4. The spinal implant as set forth in claim 3, wherein the metal particles are selected from the group consisting of gold, tungsten, tantalum, platinum, titanium and a combination thereof.

5. The spinal implant as set forth in claim 4, wherein the particles have a diameter of between 10 and 100 μm.

6. The spinal implant as set forth in claim 5, wherein the particles have a maximum diameter of about 75 μm.

7. The spinal implant as set forth in claim 1 wherein the radiopaque material is metal particles.

8. The spinal implant as set forth in claim 7, wherein the metal particles are selected from the group consisting of gold, tungsten, tantalum, platinum, titanium and a combination thereof.

9. The spinal implant as set forth in claim 8, wherein the particles have a diameter of between 10 and 100 μm.

10. The implant as set forth in claim 9, wherein the metal particles have a maximum diameter of about 75 μm.

11. A polymeric implant for replacement of a part of a natural disc nucleus comprising a layered hydrogel body comprising a hydrogel material, radiopaque particles are dispersed in at least two discrete planar layers of the hydrogel body, the hydrogel body having uppermost and lowermost surfaces and an outer side surface connecting the upper and lower surfaces, the side surface for contacting a disc annulus, the two discrete planar layers of the hydrogel body having radiopaque particles extending the entire length of the layer to the outer side surface of the layered hydrogel body contacting the disc annulus surrounding the nucleus, each discrete layer containing radiopaque particles having upper and lower surfaces adjacent a layer of the hydrogel material without radiopaque particles, the upper and lowermost surfaces of the implant having no radiopaque powder the radiopaque particles in the at least two hydrogel material layers in a concentration less than 0.5 gram of radiopaque particles to 1 cubic centimeter of the hydrogel and the particles move with the layered hydrogel body structure as the implant changes geometry under load.

12. The spinal implant as set forth in claim 11 wherein there are between 3 and 5 layers of the hydrogel material containing radiopaque particles.

13. The spinal implant as set forth in claim 12 wherein the radiopaque particles are a metal.

14. The spinal implant as set forth in claim 13, wherein the metal particles are selected from the group consisting of gold, tungsten, tantalum, platinum, titanium and a combination thereof.

15. The spinal implant as set forth in claim 14, wherein the particles have a diameter of between 10 and 100 μm.

16. The spinal implant as set forth in claim 15, wherein the particles have a maximum diameter of about 75 μm.

17. The spinal implant as set forth in claim 11 wherein the layers are planar.

18. A spinal implant for replacement of a part of a natural disc nucleus comprising:
    a hydrogel structure made from layers of gelled polymeric solution, part of the hydrogel structure having powdered radiopaque material within the gelled polymeric solution wherein the implant has a plurality of discrete planar layers of the gelled polymeric solution including the powdered radiopaque material and a plurality of planar layers of the gelled polymeric solution without the powdered radiopaque material wherein at least one discrete planar layer including radiopaque material contacts a surface of the planar layer of the gelled polymeric solution not containing radiopaque material on first and second planar sides of the layer containing the radiopaque material, the at least one planar layer including radiopaque material extending the entire length of the layer between outer side surfaces of the implant which contact a disc annulus, an uppermost and lowermost surface of the implant made of a layer of gelled polymeric solution without the radiopaque material, wherein the radiopaque material is in the form of radiopaque particles which particles are in the gelled polymeric solution layer in a concentration less than 0.5 gram of radiopaque particles to 1 cubic centimeter of the polymeric solution and the particles move with the hydrogel structure as the implant changes geometry under load.

19. The spinal implant as set forth in claim 18 wherein the radiopaque material particles are metal particles of between 10 μm and 100 μm in size.

20. The spinal implant as set forth in claim 19 wherein the metal particles are selected from the group consisting of gold, tungsten, tantalum, platinum, titanium and a combination thereof.

21. The spinal implant as set forth in claim 18 wherein there are three planar layers of gelled polymeric solution containing radiopaque material.

* * * * *